United States Patent [19]
Sestelo et al.

[11] Patent Number: 6,075,015
[45] Date of Patent: *Jun. 13, 2000

[54] VITAMIN D COMPOUNDS AND METHOD OF PREPARING THESE COMPOUNDS

[75] Inventors: José P. Sestelo; Antonio Mouriño; José L. Mascareñas, all of Santiago de Compostela, Spain; Sebastianus J. Halkes, Weesp, Netherlands; Jan Zorgdrager, Weesp, Netherlands; Gerhardus D. H. Dijkstra, Weesp, Netherlands; Jan-Paul van de Velde, Weesp, Netherlands

[73] Assignee: Duphar International Research B.V., Weesp, Netherlands

[*] Notice: This patent issued on a continued prosecution application filed under 37 CFR 1.53(d), and is subject to the twenty year patent term provisions of 35 U.S.C. 154(a)(2).

[21] Appl. No.: 08/863,947

[22] Filed: May 27, 1997

Related U.S. Application Data

[60] Continuation of application No. 08/450,695, May 25, 1995, abandoned, which is a division of application No. 08/070,998, Jun. 4, 1993, Pat. No. 5,449,668.

[51] Int. Cl.$^7$ .................................................. A61K 31/59
[52] U.S. Cl. ...................... 514/167; 514/861; 514/863; 552/653; 556/443
[58] Field of Search ........................ 552/653; 514/167, 514/861, 863; 556/443

[56] References Cited

U.S. PATENT DOCUMENTS

| | | | |
|---|---|---|---|
| 4,866,048 | 9/1989 | Calverley et al. | 514/167 |
| 5,190,935 | 3/1993 | Bēndeup et al. | 514/167 |
| 5,206,229 | 4/1993 | Calverley et al. | 514/167 |
| 5,292,728 | 3/1994 | Neef et al. | 514/167 |
| 5,321,018 | 6/1994 | DeLuca | 514/167 |
| 5,342,975 | 8/1994 | DeLuca et al. | 552/653 |
| 5,374,629 | 12/1994 | Calverley et al. | 514/167 |
| 5,378,695 | 1/1995 | Calverley et al. | 514/167 |
| 5,401,731 | 3/1995 | Caluerley et al. | 514/167 |
| 5,401,732 | 3/1995 | Calverley et al. | 514/167 |
| 5,430,196 | 7/1995 | DeLuca et al. | 568/665 |
| 5,447,924 | 9/1995 | Bretting | 514/167 |
| 5,459,136 | 10/1995 | Deluca et al. | 514/167 |

FOREIGN PATENT DOCUMENTS

| | | |
|---|---|---|
| 0521550 | 1/1993 | European Pat. Off. . |
| 521550 | 1/1993 | European Pat. Off. . |
| 9400428 | 1/1994 | WIPO . |

OTHER PUBLICATIONS

Calverley, et al, "Vitamin D" in *Amtitumor Steroids* by R. T. Blickenstaff, pp 193–270 (1992).
J. Chem Soc. Perkin Trens I, de Costa, et al, (1985) pp 1331–1336.
Napoli, et al, Biochemistry; 19 (1980) pp. 2515–2521.
Sestelo, et al. J. Org. Chem, 58 (1993) pp 118–123.
Sestelo et al, J. Org. Chem., 1993, 58, pp. 118–123, "Ultra–Sonically Induced Conjugate Addition of Iodides to . . . ".
Journal of Organic Chemistry, vol. 58, No. 1, Jan. 1, 1993, Easton, U.S., pp. 118–123, J.P. Sestelo et al., "Ultrasonically induced conjugate addition of iodides to electron–deficient olefins and its application to the synthesis of side–chain analogs of the hormone 1–alpha–25–dihydroxyvitamin D3".

*Primary Examiner*—Peter O'Sullivan
*Attorney, Agent, or Firm*—Stevens, Davis, Miller & Mosher, L.L.P.

[57] ABSTRACT

Vitamin $D_3$ analogues of the formula (I):

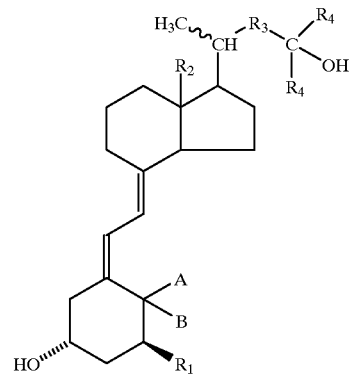

wherein $R_1$ is hydrogen or hydroxy, $R_2$ is $(C_1-C_3)$alkyl, hydroxy$(C_1-C_3)$alkyl, $(C_1-C_2)$alkoxymethyl, $(C_2-C_3)$alkenyl, or $(C_2-C_3)$alkynyl, $R_3$ is a branched or unbranched, saturated or unsaturated aliphatic 3- to 5- membered hydrocarbon or oxahydrocarbon biradical, having at least 3 atoms in the main chain and being optionally substituted with one or more substituents selected from epoxy, fluoro and hydroxy, $R_4$ is sec. or tert. $(C_3-C_6)$alkyl or $(C_3-C_6)$ cycloalkyl, A and B are each individually hydrogen or methyl, or A and B together from methylene. The compounds of the present invention exhibit pharmacotherapeutic activities, including in particular, the treatment of osteoporosis, renal osteodystrophy, osteomalacia, skin disorders such as psoriasis and other hyperproliferative skin diseases, eczema and dermatitis, nmyopathy, leukemia, breast and colon cancer, osteosarcomas, squamous cell carcinomas, melanoma, certain immunological disorders, and transplant rejections. Several methods of synthesis, including reaction of an ester compound of general formula (IX) with an inorganometallic compound of formula (III) followed by deprotection or, alternatively, first finalization of the $C_{17}$-side chain are also disclosed.

15 Claims, 2 Drawing Sheets

VITAMIN D COMPOUNDS AND METHOD OF PREPARING THESE COMPOUNDS

This application is a Continuation of application Ser. No. 08/450,695, filed May 25, 1995 now abandoned, which is a division of application Ser. No. 08/070,998, filed Jun. 4, 1993. now U.S. Pat. No. 5,499,668.

SUMMARY OF THE INVENTION

The invention relates to new vitamin D compounds, to a method of preparing these compounds and to their use in pharmacotherapy and cosmetics. The invention further relates to valuable new intermediates.

It is generally known, that vitamin-D compounds or vitamin-D related compounds ("vitamin-D compounds") have a strong biological activity and may be used in all those cases in which problems with the calcium metabolism play a part. A few years ago it was found that various active vitamin-D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications, and for diagnostic purposes.

Vitamin D compounds which are of interest for the above applications are hydroxylated vitamin D compounds, in particular vitamin D compounds hydroxylated in the 1α-, 24- and/or 25-positions. Recent developments in the field of active vitamin D compounds are 19-nor-vitamin D compounds (EP-A-0387077) and $C_{18}$-modified vitamin D compounds (EP-A-0521550), preferably also hydroxylated in the 1α-position and optionally in the $C_{17}$-side chain. Other modifications of the $C_{17}$-side chain have been proposed, likewise to improve the intended activity and to suppress detrimental side-effects. Examples of modifications of the $C_{17}$-side chain are chain elongations (homo compounds), 22-oxa modifications, fluor substitutions, epoxy groups (e.g. WO 92/21695), etc. In addition certain 24-cyclopropyl-modified vitamin D compounds are disclosed in literature, e.g. in WO 87/00834 (for treating abnormal cell differentiation and proliferation) and in an article by Farach-Carson et al. in Endocrinology 1991, 129, 1876–84. Generally, however, the above $C_{17}$-side chain modified vitamin D compounds are still not completely satisfactory as regards their selective activity, i.e. the intended activity without detrimental side-effects.

Further, the accessibility of the $C_{17}$-side chain modified vitamin D compounds is often insufficient or unattractive. As an example, the preparation of the above vitamin D compound disclosed by Farach-Carson et al, seems very laborious, while the $C_{17}$-side chain build-up, described in the above WO 87/00834, also requires various laborious synthetic steps, using a not readily available ketone as a synthon. In this connection there is a need for better accessible $C_{17}$-side chain modified vitamin D compounds. As a matter of fact, both the starting compounds for the preparation of such vitamin-D compounds must be easily available or accessible, and the multistep preparation process must lead to the intended purpose with sufficient selectivity and efficiency.

It is therefore the objective of the present invention to provide a new class of vitamin D compounds, which is well accessible from readily available or accessible starting materials.

Figure 1:
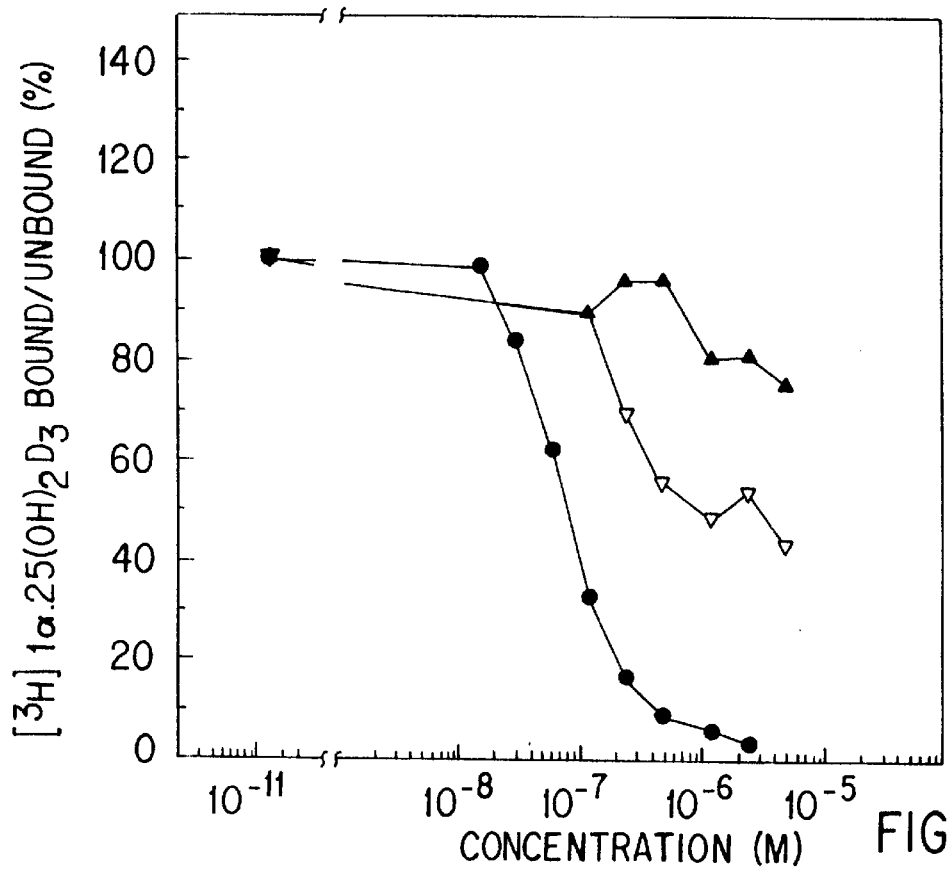
FIGS. 1 and 2 show the binding of vitamin D compounds to human vitamin D binding proteins, as per Example VIII.

According to the present invention this objective can be achieved with a new vitamin D compound of the general formula

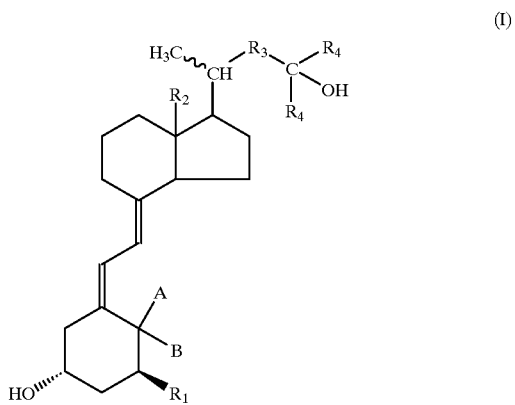

wherein:

$R_1$ is a hydrogen atom or a hydroxy group;

$R_2$ is a ($C_1$–$C_3$)alkyl group, a hydroxy($C_1$–$C_3$)alky group, a ($C_1$–$C_2$)alkoxymethyl group or a ($C_2$–$C_3$)alkenyl or alkynyl group;

$R_3$ is a branched or non-branched, saturated or unsaturated aliphatic 3- to 5-membered hydrocarbon or oxahydrocarbor biradical, having at least 3 atoms in the main chain and being optionally substituted with one or more substituents selected from epoxy, fluoro and hydroxy;

$R_4$ is a sec. or tert. ($C_3$–$C_6$)alkyl group or a ($C_3$–$C_6$) cycloalkyl group; and A and B are each individually hydrogen atoms or methyl groups, or A and B form together a methylene group.

The above new vitamin D compounds of the invention, presented by the general formula I, are valuable substances. The biological results, as illustrated in the Examples, indicate that these compounds are promising as biologically active substances and may be used in all above-mentioned pharmacotherapeutic indications, more in particular for the treatment of osteoporosis, renal osteodystrophy, osteomalacia, skin disorders such as psoriasis (and other hyperproliferative skin diseases), eczema and dermatitis, myopathy, leukemia, breast and colon cancer, osteosarcomas, squamous cell carcinomas, melanoma, certain immunological disorders, and transplant rejections.

Furthermore, the new vitamin D compounds of the invention may be used for wound healing and may be incorporated in cosmetic compositions, such as creams, lotions, ointments and the like, in order to preserve, condition and/or protect the skin and to improve various skin conditions, such as wrinkles, dry skin, skin slackness and insufficient sebum secretion. The new vitamin D compounds may also be used for diagnostic purposes.

Suitable examples of the above substituent $R_4$ are: isopropyl, cyclopropyl, tert.-butyl, thexyl (1,1,2-trimethylpropyl), 3-pentyl and cyclopentyl.

A vitamin D compound is preferred, having the above general formula I, wherein:

$R_1$ is a hydroxy group;

$R_2$ has the meaning given above;

$R_3$ is a biradical of the formula

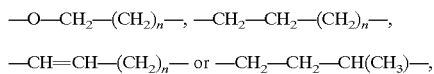

wherein n is 1 or 2;

$R_4$ is an isopropyl group, a cyclopropyl group or a tert.-butyl group; and

A and B are hydrogen atoms or form together a methylene group.

Examples of pre-eminently suitable vitamin D compounds according to the invention are vitamin D compounds of the above general formula I, wherein the symbols $R_1$, $R_2$, $R_3$, A and B have the above-defined meanings, and $R_4$ is an isopropyl group; because of their extremely favourable biological properties.

It is a special merit of the present invention that the above new vitamin D compounds of the invention can easily be prepared from readily available starting materials. In particular, it has been found, that the desired $C_{25}$-configuration, i.e. the attachment of the appropriate substituents to $C_{25}$, can easily be achieved by starting from a readily accessible ester compound.

Consequently, the invention also relates to a method of preparing a vitamin D compound of the general formula I, as defined above, wherein $R_1$ is a hydroxy group, which method is characterized according to the present invention, in that an ester compound of the general formula

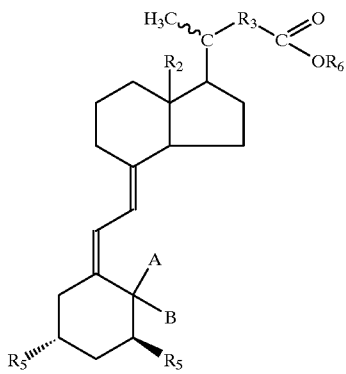
(IX)

wherein:

$R_2$, $R_3$, A and B have the above-defined meanings, $R_5$ is a protected hydroxy group, and $R_6$ is a $(C_1-C_6)$alkyl group;

is reacted with an organometallic compound of the general formula $$R_4M(X)_p \quad \text{(III)}$$

wherein:

$R_4$ has the above meaning,

X is Cl, Br or I,

M is a metal selected from Li and Mg, and p is, dependent on the valence of M, 0 or 1;

followed by deprotection.

In an equally attractive manner the $C_{17}$-side chain can first be finalized. Therefore the invention also relates to a method of preparing a vitamin D compound as defined above, which method is characterized according to the present invention, in that an ester compound of the general formula

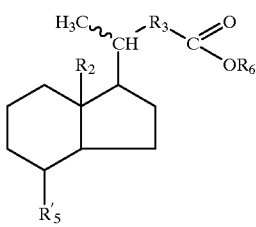
(II)

wherein:

$R_2$, $R_3$ and $R_6$ have the above meanings, and $R_5'$ is an optionally protected hydroxy group;

is reacted with an organometallic compound of the general formula $$R_4M(X)_p \quad \text{(III)}$$

wherein the symbols have the above meanings;

after which the hydrindane compound obtained, having the general formula

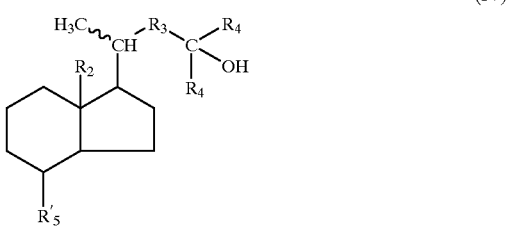
(IV)

is deprotected, if $R_5'$ is a protected hydroxy group, and then oxidized to the corresponding hydrindane-4-one compound of the general formula

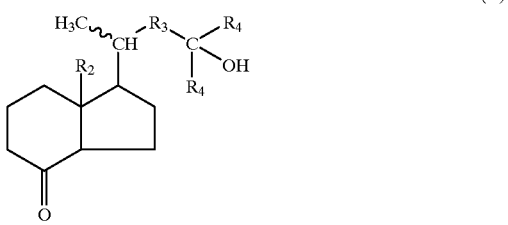
(V)

which compound of formula V, if desired after protection of the hydroxy group, is then converted either (a) with a Wittig reagent of the general formula

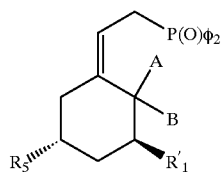
(VI)

wherein
R₁' is a hydrogen atom or a protected hydroxy group, and the other symbols have the above meanings;
or (b), after enolization and derivatization of the enolic hydroxy group, with an enyne compound of the general formula

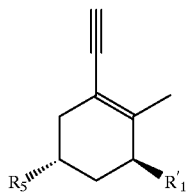
(VII)

wherein
the symbols have the above meanings, followed by hydrogenation and isomerization, to produce a compound of the general formula I, wherein A and B form together a methylene group;
followed by deprotection.

Hydroxy groups in the above intermediates or reactants may be protected by a reaction with a suitable esterification or etherification agent. A suitable esterification agent is an alkylchlorocarbonate having 2 to 5 carbon atoms, or an aromatic carboxylic acid or saturated aliphatic carboxylic acid having 1 to 4 carbon atoms such as benzoic acid, or a derivative of such acids suitable for the esterification reaction. In order to protect hydroxy groups in the form of an ether, in principle any etherification agent known for this purpose is suitable: for example, a trialkylsilylimidazole, a trialkylsilylhalide, a trialkylsilyltriflate (-trifluoromethanesulfonate), a diphenylalkylsilylhalide, or a diphenylalkylsilyltriflate, or a derivative thereof, the alkyl groups of which have 1 to 6 carbon atoms.

Particularly suitable for this purpose are trimethylsilylchloride, tert.-butyldimethylsilylchloride, dimethyl-(1,1,2-trimethylpropyl)-silylchloride, tert.-butyldimethylsilyl triflate, or trimethylsilylimidazole, because these etherification agents readily react with the hydroxy group to be protected to form an ether function, which on the one hand is sufficiently stable under the conditions of the reaction or reactions in view, but on the other hand can easily be removed [deprotection] to recover the original hydroxy group); tert.-butyldimethylsilylchloride or triflate is to be preferred, because the tert.-butyldimethylsilyl group has been found to be excellently suitable as a protective group.

The enolic hydroxy group is preferably derivatized by a reaction with N-phenyltriflimide to produce a triflate.

The starting compounds of formula II can conveniently be prepared from readily available substances, e.g. for the synthesis of vitamin D compounds with the above-defined preferred C₁₇-side chains as follows:

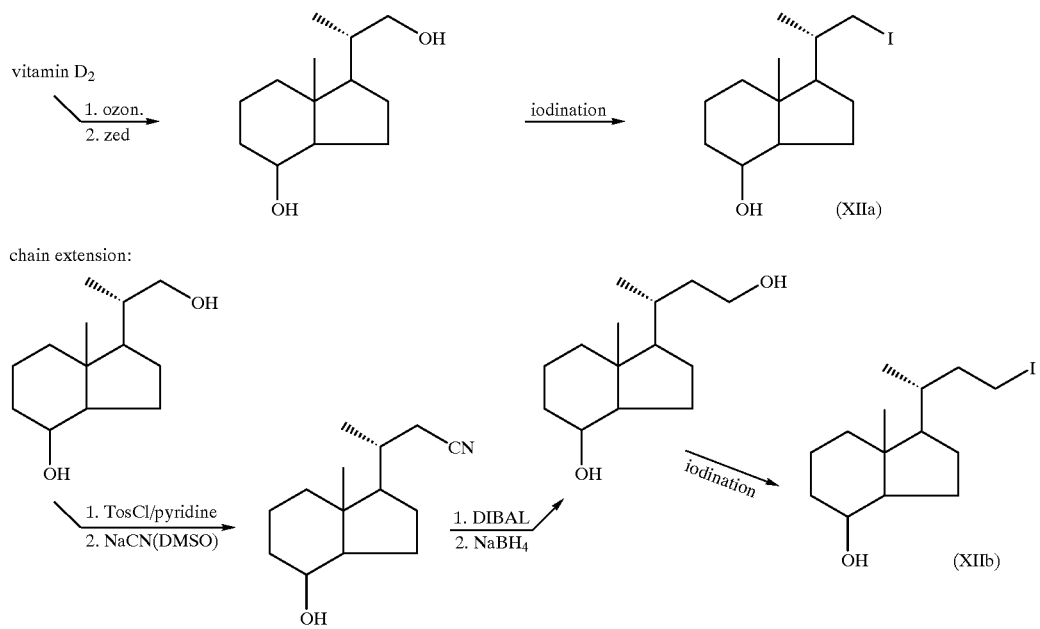

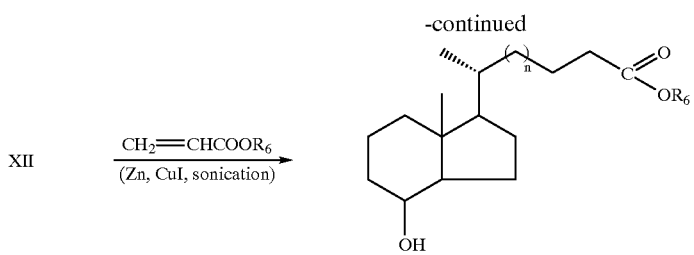

The introduction of a $C_{18}$ modification ($R_2$) into the vitamin D compound of the invention can conveniently be achieved as described in the above-mentioned EP-A-0521550.

Suitable examples of organometallic compounds of the above general formula III are lithium compounds, such as isopropyllithium, cyclopropyllithium and tert.-butyllithium, and Grignard reagents, such as isopropylmagnesium chloride, cyclopropylmagnesium chloride and tert.-butylmagnesium chloride, as well as the corresponding bromides.

The intermediate ester compound of the general formula IX, presented above, is new. Therefore the present invention also relates to this intermediate, as well as to a method of preparing this compound.

The ester compound of the general formula IX, wherein A and B form together a methylene group, can conveniently be prepared by reacting an ester of the general formula

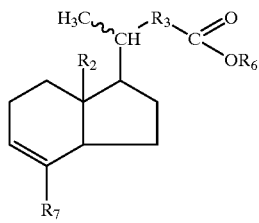

(VIII)

wherein:
$R_2$, $R_3$ and $R_6$ have the above meanings, and
$R_7$ is a derivatized hydroxy group,
is reacted with an enyne compound of the general formula

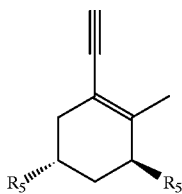

(VII-A)

wherein
the symbols have the above meanings;
followed by hydrogenation and isomerization.

This reaction is preferably carried out in two reaction steps, viz. by first reacting the ingredients under the influence of an organic base such as triethylamine, and in the presence of a palladium catalyst such as $(PPh_3)_2PdCl_2$, and by then subjecting the product obtained to a hydrogenation with hydrogen under the influence of a suitable catalyst such as Lindlar catalyst (Pd on $CaCO_3$, poisoned with lead), followed by an isomerization of the previtamin configuration obtained to the vitamin structure of the general formula IX.

Alternatively, said ester compound of the general formula IX can easily be synthetized by reacting a modified Windaus Grundmann ketone of the general formula X or XI with a Wittig reagent as follows:

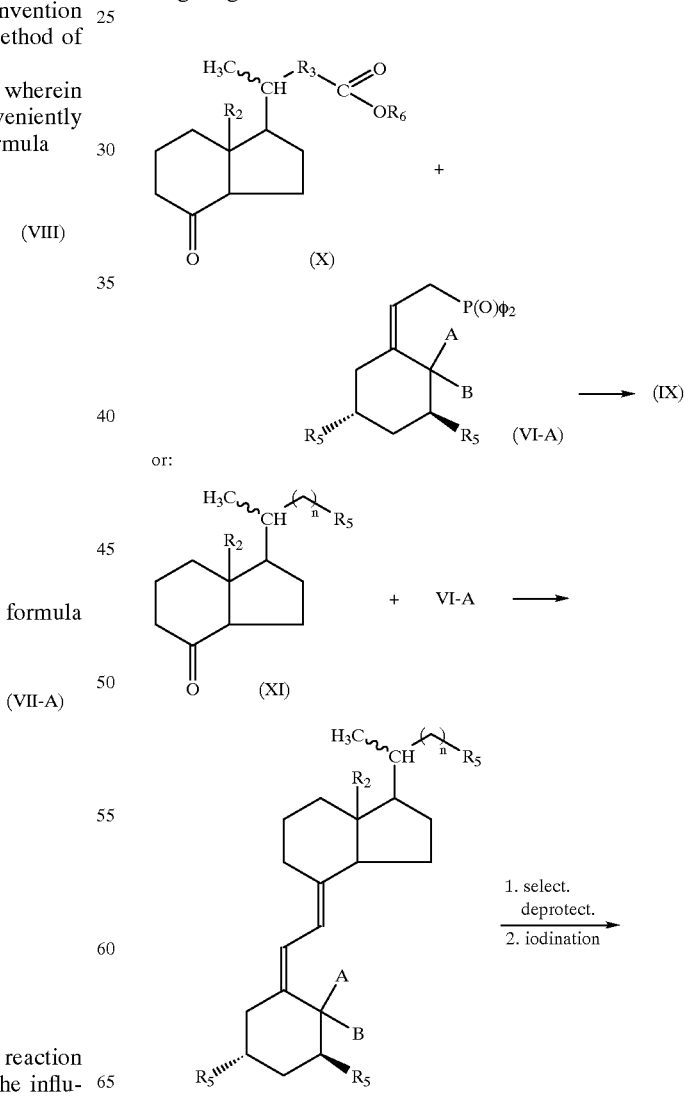

-continued

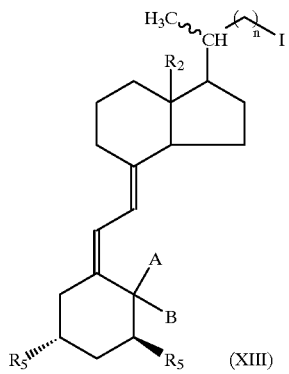

(XIII)

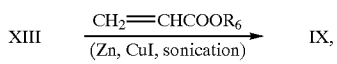    IX, wherein $R_3 = (CH_2)_3$ or $(CH_2)_4$.

The symbols in the above formulas are defined hereinbefore. The intermediate hydrindane-4-one compound of the general formula V, presented above, is new. Therefore the present invention also relates to this intermediate and to a method of preparing this compound, viz. by oxidizing a hydrindane compound of the general formula IV, as defined above, with an oxidizing agent, preferably selected from a chromium-containing oxidant such as pyridinium chlorochromate or pyridinium dichromate, and ruthenium tetroxide.

The intermediate hydrindane compound of the general formula IV, presented above, is also new. Consequently, the present invention relates in addition to this intermediate and to a method of preparing this compound, viz. by reacting a compound of the general formula II, as defined above, with a metal-organic compound of the general formula III, as also defined above, in an inert organic solvent.

To improve the applicability of the new vitamin D compounds of the invention for the above-described pharmacotherapeutic indications, the compounds are usually processed to pharmaceutical compositions, comprising an effective amount of said vitamin D compound as the active ingredient in addition to a pharmaceutically acceptable carrier and/or at least one pharmaceutically acceptable auxiliary substance. Such a composition may be delivered in a dosage unit form for oral, topical (dermal) or parenteral administration, comprising approx. 0.1 µg to approx. 0.1 mg active ingredient per dosage unit. A composition for diagnostic purposes may comprise, in addition to the vitamin D compound of the present invention, a compatible, non-toxic carrier and/or at least one auxiliary substance. A cosmetical composition may comprise, in addition to an effective amount (in the range of approx. 0.1 µg to approx. 0.1 mg per dosage unit in a dosage unit form) of the vitamin D compound of the present invention, a cosmetically acceptable, non-toxic carrier and/or at least one auxiliary substance.

Finally the invention relates to a method for the treatment and prophylaxis of a number of disease states including autoiummune diseases (including diabetes mellitus), acne, alopecia, skin aging (including photo-aging), imbalance in the immune system, inflammatory diseases such as rheumatoid arthritis and asthma, as well as diseases related to abnormal cell differentiation and/or proliferation, in a warm-blooded living being, comprising administering to said being or treating said being with a pharmaceutical composition as defined above in a quantity effective for the intended purpose. Examples of such diseases are psoriasis and other hyperproliferative skin diseases. The present invention also relates to the use of the above pharmaceutical compositions for the treatment of solid, skin and blood cancers, in particular of blood cancers such as leukemia, of breast cancer, and of skin cancers such as melanoma and squamous cell carcinoma.

The above-defined cosmetical compositions, in particular selected from the group consisting of creams, lotions, ointments, liposomes and gels, can be used for the treatment and prevention of a number of skin disorders, such as inadequate skin firmness or texture, insufficient skin hydration, wrinkles and insufficient sebum secretion.

The invention will now be described in greater detail with reference to the following specific Examples.

EXAMPLES

Example I

Preparation of Vitamin Ester

Reaction Equation:

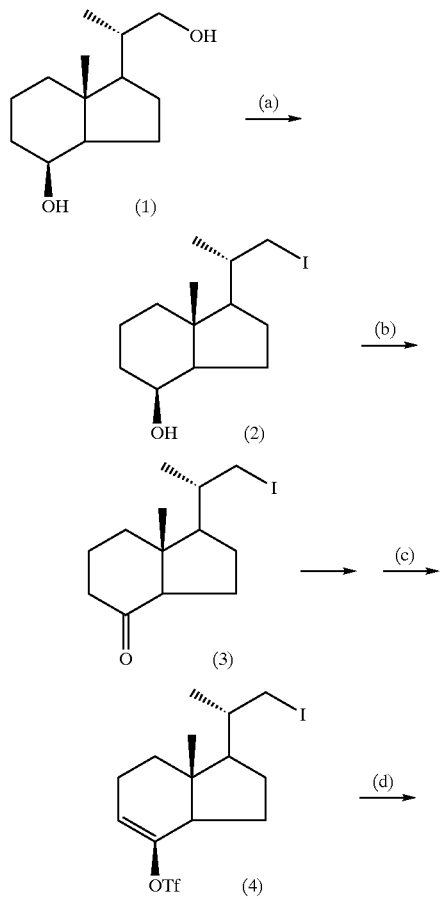

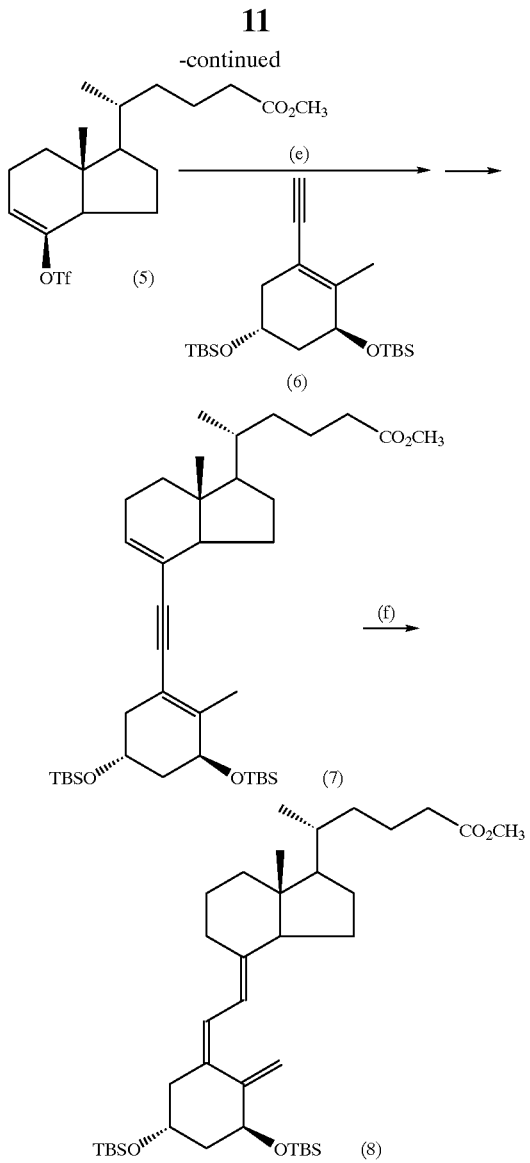

(a). Ph$_3$P (6.5 g) and imidazole (4.8 g) are added to a solution of diol (1) (5.0 g) in THF (100 ml). The suspension is cooled to −20° C., and I$_2$ (6.28 g) is added in portions. After being stirred for 15 min, the reaction mixture is warmed to room temp., further stirred for 15 min., cooled to 0° C., and poured into saturated aqueous NaHCO$_3$ (50 ml). The mixture is extracted with Et$_2$O and the extract is washed with saturated aqueous Na$_2$S$_2$O$_3$ and H$_2$O, dried and filtered. Concentration affords a residue which is purified by flash chromatography (8% EtoAc/hexane) to give 7.32 g of iodide (2). After crystallization from EtOAc/hexane, the product has a melting point of 51° C.; identification by NMR and elem. analysis.

(b). Pyridinium dichromate (8.66 g) is added to a solution of compound (2) (3.99 g) in 50 ml CH$_2$Cl$_2$. The mixture is stirred for 6 h at room temp. Et$_2$O (60 ml) is added, and the resulting suspension is stirred for 15 min and filtered. The filtrate is washed with brine, dried, filtered and concentrated. Purification by flash chromatography (10% EtOAc/hexane) gives the desired iodo ketone (3) in a yield of 3.57 g; crystallization from Et$_2$O/hexane: m.p. 65° C. Identification by NMR and elem. analysis.

(c). Lithium diisopropylamine is prepared by addition of i-Pr$_2$NH (3.9 mmol) to a cooled (−78° C.) solution of n-BuLi in hexane (3.5 mmol in 1.43 ml). After stirring for 10 min, the mixture is diluted with THF (4 ml), stirred at 0° C. for 30 min, and cooled to −78° C. A solution of ketone (3) (1.0 g) in 14 ml THF is slowly added, followed by a solution of N-phenyltriflimide (1.225 g) in 4 ml THF. The mixture is stirred for 2 h at −78° C. After being warmed to 0° C., the reaction is quenched by addition of a few drops of MeOH and water. Concentrazion gives a crude product which is diluted with EtOAc/hexane (30 ml), washed with brine, dried, filtered and concentrated. The resulting residue is purified by flash chromatography (2% EtOAc/hexane), affording 1.29 g of the iodo triflate (4) as a colourless oil. Identification by NMR and elem. analysis.

(d). A suspension of CuI (201 mg) and Zn (161 mg) in EtOH/H$_2$O (6 ml 7:3; deoxygenated) is sonicated for 5 min. Methyl acrylate (637 μl, freshly distilled), and a solution of the iodide (4) (160 mg) in EtOH/H$_2$O (1 ml 7:3) are successively added, and the resulting mixture is sonicated for 40 min. Dilution with Et$_2$O (15 ml) and filtration gives a solution that is washed with brine. The aqueous phase is extracted with Et$_2$O (30 ml) and the combined organic extracts are dried, filtered and concentrated. Flash chromatography of the residue (6% EtOAc/hexane) affords 96 mg of the methyl ester (5) (colourless oil). Identification by NMR and elem. analysis.

(e). The palladium-catalyzed coupling between vinyl triflate (5) and the enyne (6) is performed as follows:

A mixture of enyne (6) (507 mg), triflate (5) (500 mq), Et$_3$N (4.85 mmol) and (Ph$_3$P)$_2$PdCl$_2$ (16 mg) in 21 ml DMF is heated at 75° C. for 1 h. The mixture is cooled to room temp., diluted with EtOAc/hexane (50 ml 1:3), and washed with brine. Drying, filtration and concentration gives a residue which is purified by flash chromatography (2–4% Et$_2$O/hexane) to afford 675 mg of dienyne (7) (viscous liquid). Identification by NMR.

(f). Product (7) is hydrogenated by Lindlar catalyst as follows:

A solution (0.2 ml) of 50 μl quinoline in 10 ml hexane is added to a solution of dienyne (7) (305 mg) in 12 ml hexane. Lindlar catalyst (50 mg), previously dried, is added and the resulting solution is exposed to hydrogen gas at atmospheric pressure. After stirring for 8 h, the reaction mixture is filtered and concentrated. The residue is purified by flash chromatography (1–3% Et$_2$O/hexane) to give 295 mg of the protected previtamin D compound.

Isomerization of previtamin D compound to vitamin D compound (8):

The previtamin D compound obtained (295 mg) is dissolved in 15 ml isooctane and refluxed in the dark for 5 h. Concentration gives a residue which is purified by flash chromatography (2–4% Et$_2$O/hexane) to afford 290 mg of compound (8). the product is identified by $^1$H-NMR, $^{13}$C-NMR and elem. analysis.

$^1$H-NMR (δ, CDCl$_3$): 6.24 and 6.02 (d, 2H), 5.18 (m, 1H), 4.87 (m, 1H), 4.37 (m, 1H), 4.18 (m, 1H), 3.67 (s, 3H), 0.93 (d, 3H), 0.88 (s, 18H), 0.53 (s, 3H), 0.07 (s, 12 H). $^{13}$C-NMR (δ, CDCl$_3$): 173.1, 148.4, 141.0, 135.0, 132.2, 118.0, 111.2, 72.1, 67.5, 56.3, 51.3, 46.0, 45.7, 44.8, 40.6, 35.8, 35.3, 34.4, 31.5, 28.8, 27.6, 25.8, 25.7, 23.4, 22.6, 22.1, 21.5, 18.7, 18.1, 18.0, 14.0, 11.9, −4.8, −4.8, −4.9, −5.2.

Elem. anal.: Calcd. for C$_{38}$H$_{66}$O$_4$Si$_2$: C, 70,75; H, 10.62. Found: C, 70.42; H, 10.43.

In a corresponding manner the following ester compounds are prepared: general formula

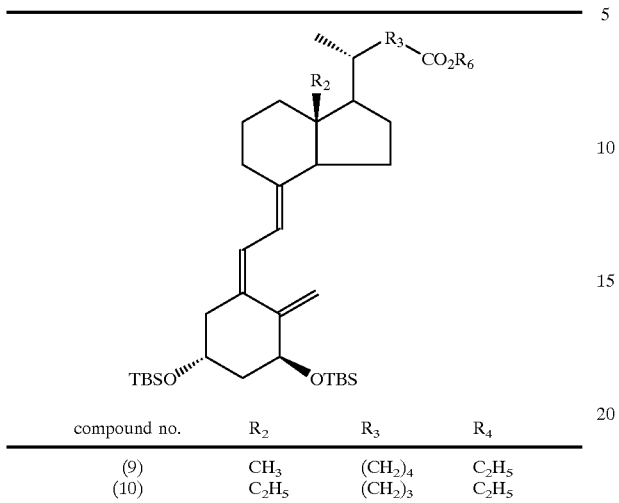

| compound no. | R₂ | R₃ | R₄ |
|---|---|---|---|
| (9) | CH₃ | (CH₂)₄ | C₂H₅ |
| (10) | C₂H₅ | (CH₂)₃ | C₂H₅ |

Compd. (9): This 24-homo compound is prepared by using in the above step (a) as the starting substance a homologue of compd. (1), having a 1-methyl-3-hydroxypropyl side chain; in step (d) ethyl acrylate is used as the olefin.

$^1$H-NMR ($\delta$, CDCl₃): 0.08 (s, 12H), 0.52 (s, 3H), 0.87 (s, 18H), 0.90 (d, 3H), 1.25 (t, 3H), 4.11 (q, 2H), 4.20 (m, 1H), 4.37 (m, 1H), 4.87 (d, 1H), 5.18 (d, 1H), 6.01 (d, 1H), 6.24 (d, 1H);

Compd. (10): This 18-homo compound is prepared by using in the above step (a) as the starting compound a homologue of compd. (1), prepared as described in published European patent application 521550 [compound no. (64)].

$^1$H-NMR ($\delta$, CDCl₃): 0.87 (s, 6H), 0.88 (t, 3H), 1.01 (d, 3H), 1.25 (t, 3H), 1.98 (t, 1H), 2.25 (m, 2H), 2.44 (dd, 1H), 4.13 (q, 2H), 4.18 (m, 1H), 4.37 (m, 1H), 4.86 (s, 1H), 5.17 (s, 1H), 6.01 (d, 1H), 6.23 (d, 1H).

Example II
Preparation of Vitamin D Compound from Vitamin Ester
Reaction Equation:

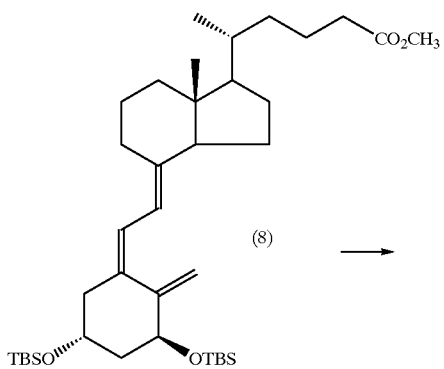

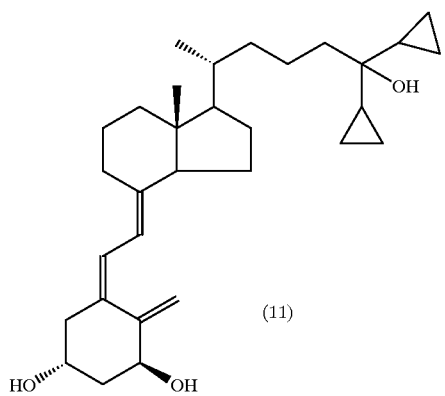

Compound (11) is prepared as follows: Cyclopropyl bromide (0.51 mmol) is slowly added to a cooled (−20° C.) solution of t-BuLi in Et₂O (0.51 mmol in 0.602 ml), to produce cyclopropyllithium. The resulting mixture is warmed to room temp. and diluted with 2.4 ml Et₂O. 1 ml of this solution is slowly added to a cooled (−78° C.) solution of compd. (8) (50 mg) in 3 fl Et₂O. The reaction mixture is allowed to come to −40° C. and quenched with a few drops of water. The resulting solution is diluted with Et₂O, washed with brine, dried, filtered and concentrated. The concentrate is filtered through a flash chromatography column (2% Et₂O/hexane), affording a product (46 mg) which is dissolved in 7 ml THF and stirred in the dark at room temp. with tetrabutyl ammoniumfluoride in THF (0.36 mmol in 0.36 ml) for 24 h. Concentration gives a residue which is diluted with EtOAc (20 ml), dried, filtered, concentrated and flash chromatographed (60% EtOAc/hexane) to give 23 mg of the desired compound (11) as a white solid.

$^1$H-NMR ($\delta$, CD₂Cl₂): 6.44 and 5.99 (d, 2H), 5.27 (br-d, 1H), 4.95 (br-d, 1H), 4.35 (m, 1H), 4.15 (m, 1H), 0.92 (d, 3H), 0.81 (m, 2H), 0.53 (s, 3H), 0.34 (m, 8H); $^{13}$C-NMR ($\delta$, CD₂Cl₂): 148.6, 143.5, 133.9, 125.1, 117.6, 111.8, 71.2, 71.0, 67.2, 57.2, 56.8, 45.8, 43.5, 43.4, 41.0, 37.1, 36.6, 29.4, 28.0, 24.0, 22.6, 20.8, 19.0, 12.1, 0.8, −0.5.

In a corresponding manner the following vitamin D compounds are prepared:
Deneral Formula

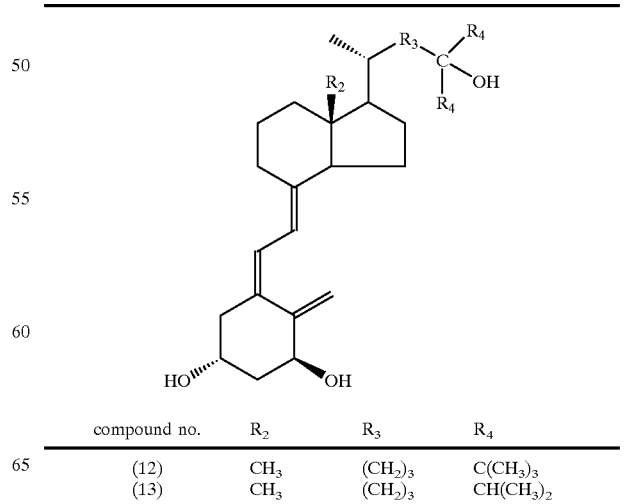

| compound no. | R₂ | R₃ | R₄ |
|---|---|---|---|
| (12) | CH₃ | (CH₂)₃ | C(CH₃)₃ |
| (13) | CH₃ | (CH₂)₃ | CH(CH₃)₂ |

15

-continued

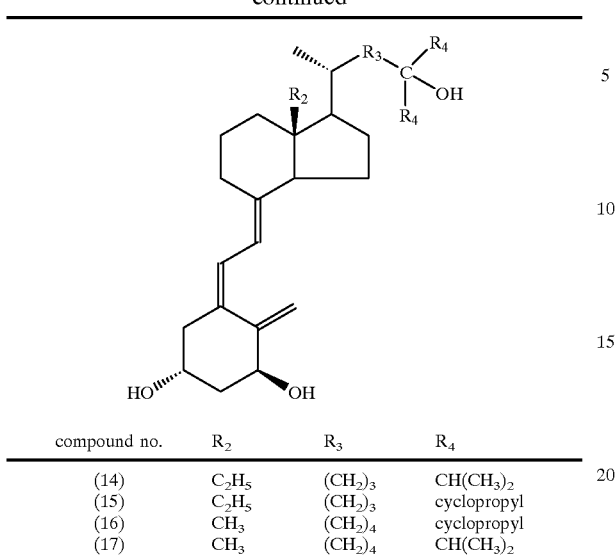

| compound no. | $R_2$ | $R_3$ | $R_4$ |
|---|---|---|---|
| (14) | $C_2H_5$ | $(CH_2)_3$ | $CH(CH_3)_2$ |
| (15) | $C_2H_5$ | $(CH_2)_3$ | cyclopropyl |
| (16) | $CH_3$ | $(CH_2)_4$ | cyclopropyl |
| (17) | $CH_3$ | $(CH_2)_4$ | $CH(CH_3)_2$ |

Compd. (12) is prepared by using t-butyllithium instead of cyclopropyllithium.

Compounds (13), (14) and (17) are prepared by using isopropyllithium instead of cyclopropyllithium.

Compd. (12): $^1$H-NMR ($\delta$, $CDCl_3$): 6.38 and 6.01 (d, 2H), 5.33 (m, 1H), 5.00 (m, 1H), 4.43 (m, 1H), 4.23 (m, 1H), 1.00 (s, 18H) 0.93 (d, 3H), 0.54 (s, 3H). $^{13}$C-NMR ($\delta$, $CDCl_3$): 148.7, 143.4, 134.0, 125.0, 117.6, 111.8, 80.0, 71.1, 67.1, 60.6, 56.9, 56.8, 46.3, 45.8, 43.4, 42.8, 40.9, 37.0, 36.5, 34.2, 29.4, 28.8, 28.0, 24.0, 23.3, 22.7, 19.2, 12.1.

Compd. (13): $^1$H-NMR ($\delta$, $CD_3OD$): 0.55 (s, 3H), 0.90 (m, 15H), 2.22 (dd, 1H), 2.48 (dd, 1H), 2.83 (dd, 1H), 4.09 (m, 1H), 4.31 (t, 1H), 4.86 (b?, 1H), 5.25 (b, 1H), 6.05 (d, 1H), 6.29 (d, 1H).

Compd. (14): $^1$H-NMR ($\delta$, $CDCl_3$): 0.84 (t, 3H), 0.95 (m, 12H), 1.00 (d, 3H), 2.32 (dd, 1H), 2.60 (dd, 1H), 2.83 (dd, 1H), 4.24 (m, 1H), 4.44 (m, 1H), 5.01 (b, 1H), 5.33 (b, 1H), 6.01 (d, 1H), 6.39 (d, 1H).

Compd. (15): $^1$H-NMR ($\delta$, $CD_3OD$): 0.70–0.40 (m, 8H), 0.76 (m, 2H), 0.91 (t, 3H), 1.01 (d, 3H), 2.00 (m, 1H), 2.22 (dd, 1H), 2.29 (b, 1H), 2.48 (dd, 1H), 2.83 (dd, 1H), 4.09 (m, 1H), 4.31 (t, 1H), 4.85 (b, 1H), 5.25 (b, 1H), 6.04 (d, 1H), 6.29 (d, 1H).

Compd. (16): $^1$H-NMR ($\delta$, $CD_3OD$): 0.20–0.40 (m, 8H), 0.57 (s, 3H), 0.79 (m, 2H), 0.95 (d, 3H), 2.25 (dd, 1H), 2.51 (dd, 1H), 2.86 (dd, 1H), 4.12 (m, 1H), 4.35 (t, 1H), 4.89 (b, 1H), 5.28 (b, 1H), 6.08 (d, 1H), 6.32 (d, 1H).

Compd. (17): $^1$H-NMR ($\delta$, $CD_3OD$): 0.53 (s, 3H), 0.90 (m, 12H), 2.22 (dd, 1H), 2.48 (dd, 1H), 2.83 (dd, 1H), 4.09 (m, 1H), 4.31 (t, 1H), 4.86 (b, 1H), 5.25 (b, 1H), 6.05 (d, 1H), 6.29 (d, 1H).

Example III

Preparation of 1-(1-methyl-5-hydroxy-5,5-diisopropyl-pentyl)-hydrindanol-4 (19)

16

Reaction Equation:

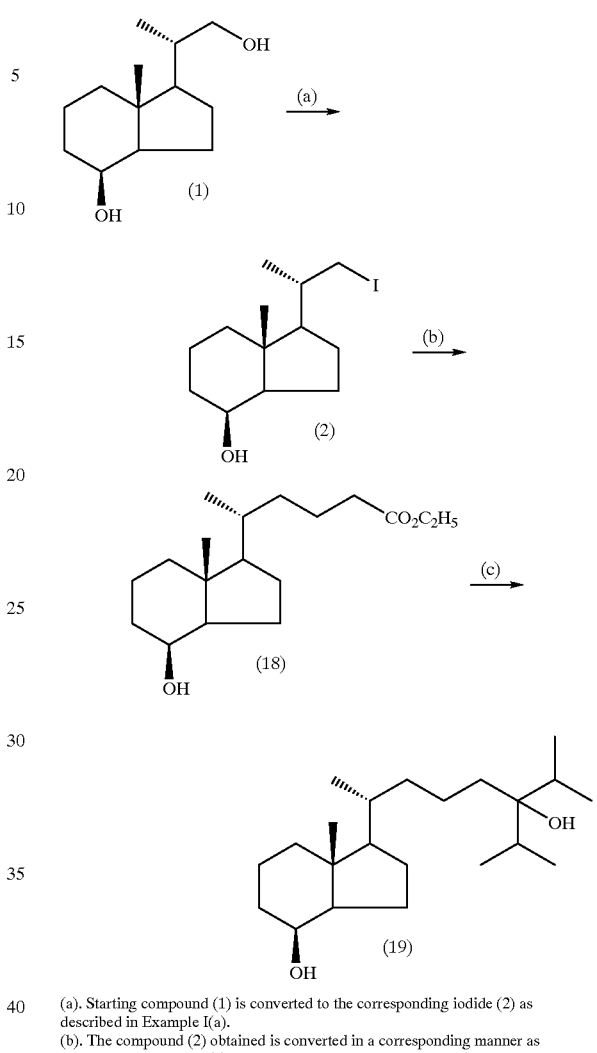

(a). Starting compound (1) is converted to the corresponding iodide (2) as described in Example I(a).
(b). The compound (2) obtained is converted in a corresponding manner as described in Example I(d), using ethyl acrylate as the olefin, to produce ester compound (18).
(c). Ester compound (18) is converted to compound (19) by a reaction with an excess of isopropyllithium, in a corresponding manner as described in Example II. The product is identified by $^1$H—NMR.

In a corresponding manner the following compounds are prepared:
General Formula

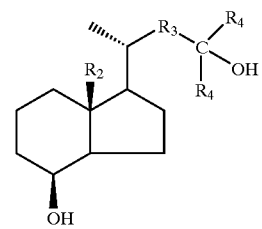

| compound no. | $R_2$ | $R_3$ | $R_4$ |
|---|---|---|---|
| (20) | $CH=CH_2$ | $(CH_2)_3$ | cyclopropyl |
| (21) | $CH=CH_2$ | $(CH_2)_3$ | isopropyl |

-continued

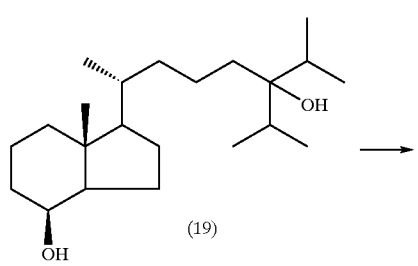

| compound no. | R$_2$ | R$_3$ | R$_4$ |
|---|---|---|---|
| (22) | CH$_3$ | (CH$_2$)$_4$ | isopropyl |
| (23) | CH$_3$ | (CH$_2$)$_4$ | cyclopropyl |

The products are identified by $^1$H-NMR.

Example IV

Preparation of 1-(1-methyl-5-hydroxy-5,5-diisopropyl-pentyl)-hydrindanone-4 (24)

Reaction Equation:

-continued

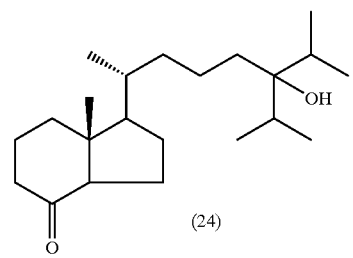

Oxidation of compound (19) by using pyridinium dichromate as the oxidant, in a corresponding manner as described in Example I(b), affords the desired ketone (24) in a yield of 84%. The product is identified by $^1$H-NMR.

In a corresponding manner the following ketones are prepared:

General Formula

| compound no. | R$_2$ | R$_3$ | R$_4$ |
|---|---|---|---|
| (25) | CH=CH$_2$ | (CH$_2$)$_3$ | cyclopropyl |
| (26) | CH=CH$_2$ | (CH$_2$)$_3$ | isopropyl |
| (27) | CH$_3$ | (CH$_2$)$_4$ | isopropyl |
| (28) | CH$_3$ | (CH$_2$)$_4$ | cyclopropyl |

The products are identified by $^1$H-NMR.

Example V

Preparation of Vitamin D Compound (13) from Ketone (24)

Reaction Equation:

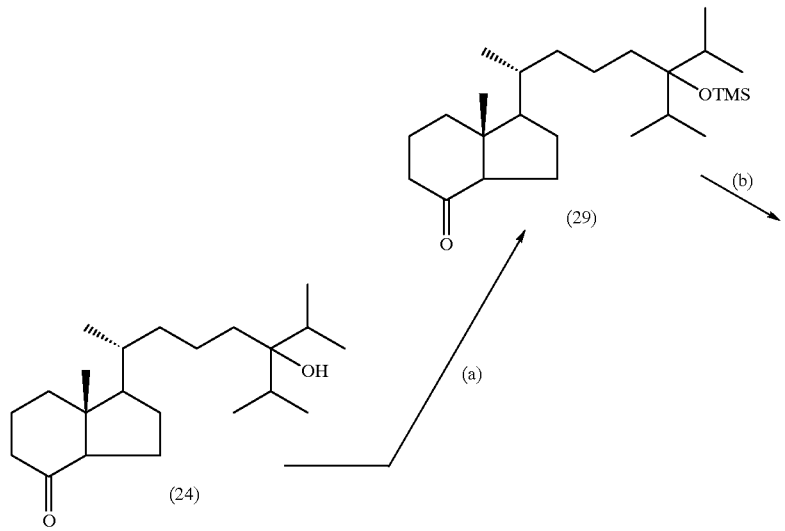

-continued

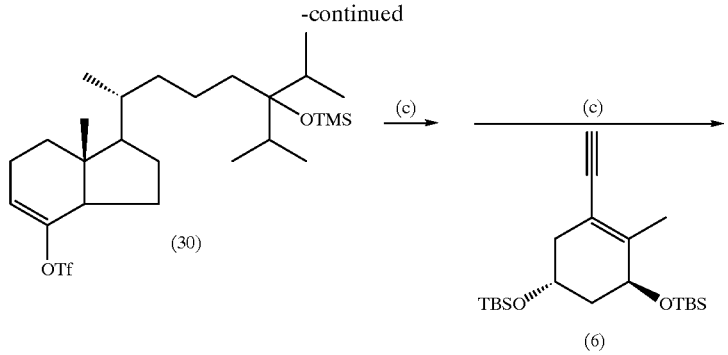

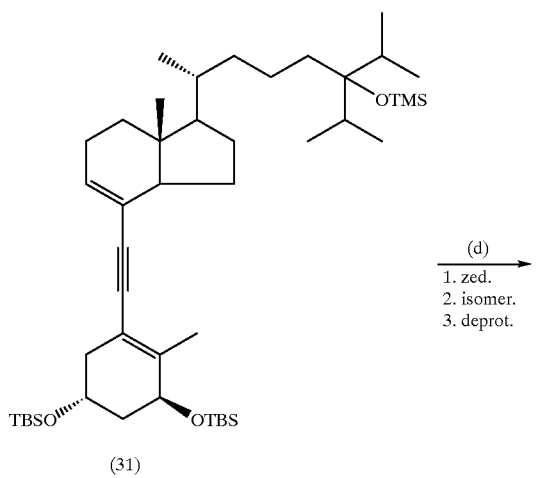

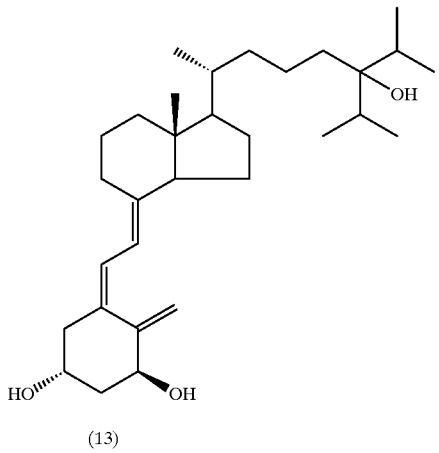

(a). The free hydroxy group is protected by a reaction with trimethylsilyltriflate (TBS-triflate) in the presence of triethylamine and in methylene chloride as the solvent; temp. -78° C. -- 0° C.; yield of compound (29) is 80%.
(b). The enolisation is carried out in a corresponding manner as described in Example I(c), producing compound (30) in a yield of 71%.
(c). In a corresponding manner as described in Example I(e), the coupling reaction with enyne (6) is performed, affording compound (31) in a yield of 94%.
(d). The final reaction step is carried out in a corresponding manner as described in Example I(f), followed by deprotection (desilylation), as described in Example II, with tetrabutyl ammoniumfluoride. The final vitamin D compound (13) is obtained in an overall yield of 65%. The product is identical with the product obtained according to Example II.

In a corresponding manner the following vitamin D compounds are prepared.

General Formula

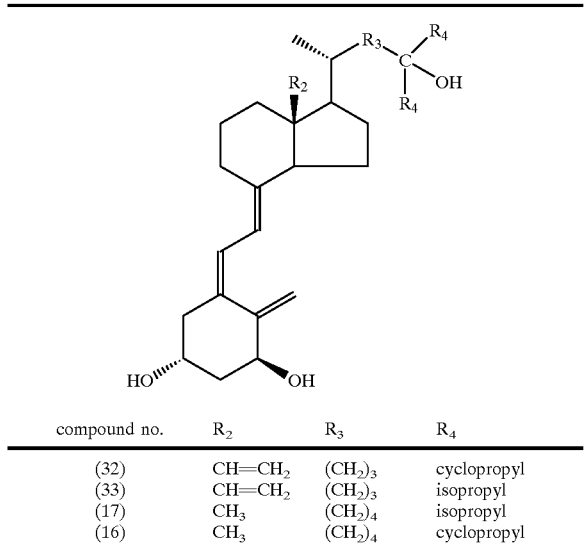

| compound no. | R₂ | R₃ | R₄ |
|---|---|---|---|
| (32) | CH=CH₂ | (CH₂)₃ | cyclopropyl |
| (33) | CH=CH₂ | (CH₂)₃ | isopropyl |
| (17) | CH₃ | (CH₂)₄ | isopropyl |
| (16) | CH₃ | (CH₂)₄ | cyclopropyl |

The products are identified by $^1$H-NMR. The last two vitamin D compounds are identical with the corresponding vitamin D compounds prepared according to Example II.

Example VI

Preparation of 19-nor-vitamin D Compound (35) from Ketone (29)

Reaction Equation:

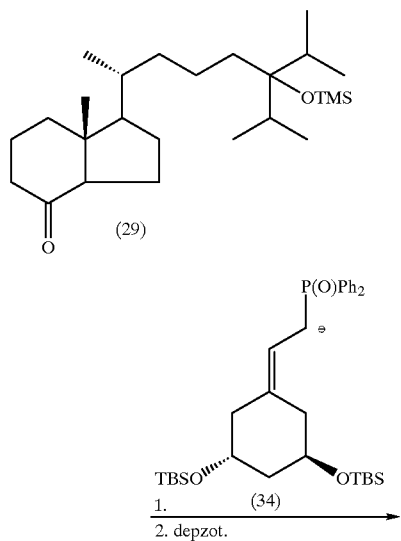

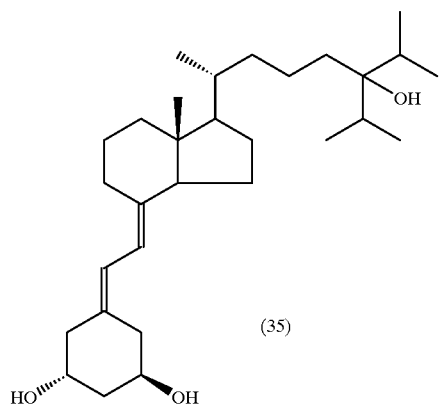

A solution of 1.14 g (2 mmol) of phosphine oxide (34) in 15 ml of dry THF is cooled to −78° C. n-Buthyllithium (BuLi), as a 2.5 M solution in hexane, is added dropwise until the red colour persists. Then 0.8 ml of a 2.5 M solution of BuLi is added. Stirring is continued for 15 min, followed by the dropwise addition of 0.73 g (1.8 mmol) of ketone (29) in 5 ml THF. After another hour of stirring, the reaction mixture is allowed to reach 0° C. and then quenched by the addition of 50 ml of a saturated NH₄Cl-solution. Extractive work-up and flash chromatography (2% EtOAc in hexane) then affords the protected diene compound. Desilylation by reaction with 10 eq. of tetrabutylammonium fluoricde (TBAF.3aq) in THF (10 ml) during 48 hours gives compound (35), which is purified by flash chromatography using EtOAc as an eluent, followed by recrystallization from MeOH/EtOAc. The overall yield is 53%. Identification by $^1$H-NMR.

In a corresponding manner the following vitamin D compounds are prepared:
General Formula

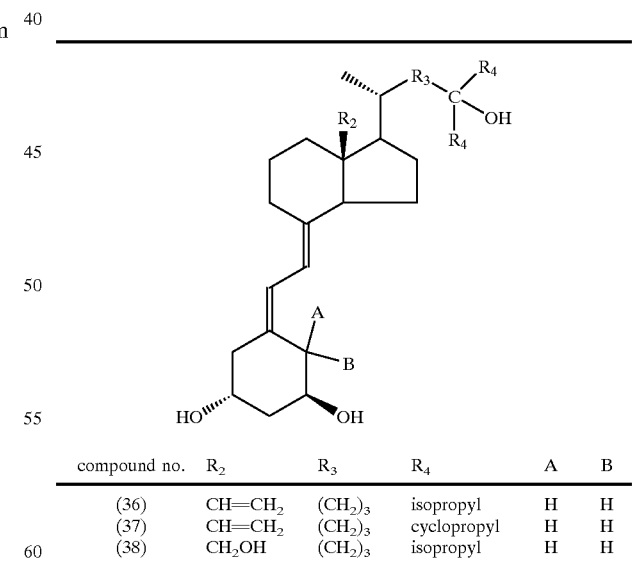

| compound no. | R₂ | R₃ | R₄ | A | B |
|---|---|---|---|---|---|
| (36) | CH=CH₂ | (CH₂)₃ | isopropyl | H | H |
| (37) | CH=CH₂ | (CH₂)₃ | cyclopropyl | H | H |
| (38) | CH₂OH | (CH₂)₃ | isopropyl | H | H |

The products are identified by $^1$H-NMR.

Example VII
Affinity to Intracellular Vitamin D Receptor

Vitamin D compounds according to the invention are dissolved in ethanol in concentrations ranging from $10^{-13}$ to $10^{-7}$ M. The affinity towards the calf thymus intracellular vitamin D receptor (VDR) is determined in a biological assay. In this assay, $^3$H-1α,25-dihydroxycholecalciferol ($^3$H-1α,25-DHCC), which is specifically bound to the VDR, is replaced by the tested compounds. Especially the tested compounds 11, 13 and 14 have a very high VDR-affinity. A high VDR-affinity is indicative for biologically active substances.

Example VIII

Affinity to Vitamin D Binding Protein

Vitamin D binding protein (DBP) is the specific carrier for vitamin D and its metabolites in blood. The biological act:vity of vitamin D compounds depends on their binding to DBP, because strong binding to DBP will reduce the intracellular access to the VDR. Birding to the DBP may also influence the half-life of the vitamin D derivatives in circulation. Weak binders are rapidly metabolized, which is a favourable aspect in topical application.

Figure 2:
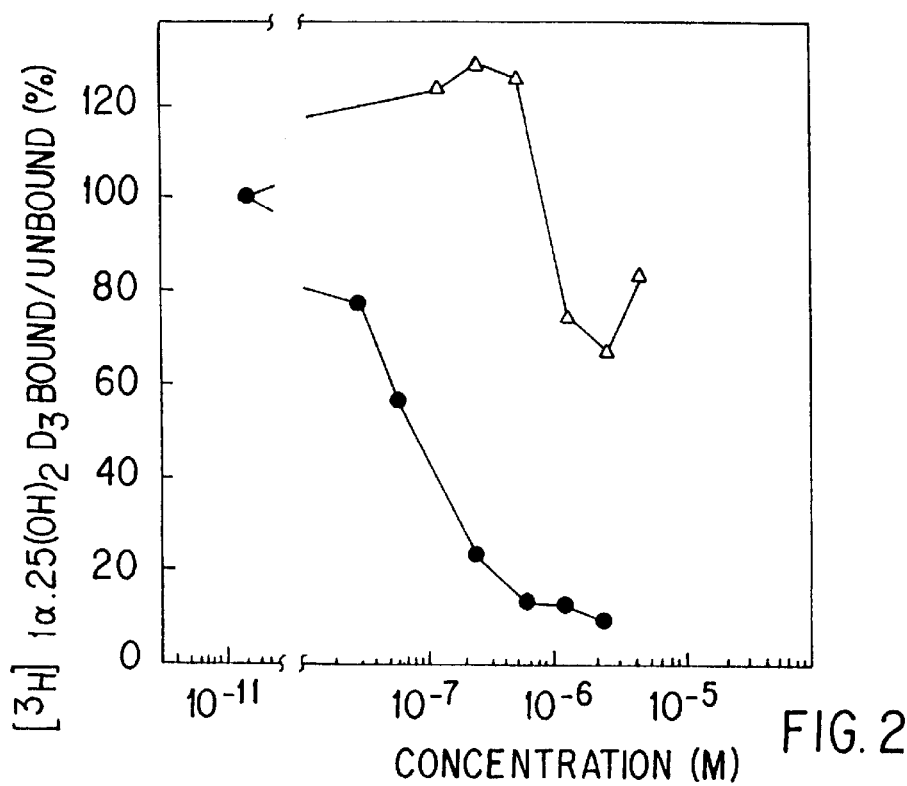

In the assay, DBP is incubated with $^3$H-1α,25-DHCC and 1α,25-DHCC or with several vitamin D compounds according to the invention. To this purpose, the vitamin compounds are dissolved in ethanol in concentrations ranging from $10^{-11}$ to $2.5 \times 10^{-6}$ M. The percentage bound/unbound $^3$H-1α,25-DHCC is then calculated. DBP is purified from total human serum. The results are shown in the appended FIGS. 1 and 2. FIGS. 1 and 2 show the binding of vitamin D compounds to human vitamin D binding protein. [$^3$H]1α, 25(OH)$_2$D$_3$=$^3$H-1α,25-DHCC; in both FIGS. ●=1α,25-DHCC (known compound); in FIG. 1 ▲=compound 13 and ▽=compound 14; in FIG. 2 Δ=compound 11.

Compounds 14 and 11 bind rather weakly to the DBP, compared to the known 1α, 25-DHCC. Compoun d 13 is a very weak binder.

Example IX

Cell Differentiation

Vitamin D compounds according to the invention are dissolved in ethanol in concentrations ranging from $10^{-12}$ to $10^{-6}$ M and tested for their capacity to induce cell differentiation in a HL-60 assay. In this assay, morphologic and biochemical examination of the human leukemic cell line HL-60 is done, in order to establish whether cell differentiation has taken place.

Differentiation is expressed as the maturation parameters nitroblue tetrazolium (NBT) reduction, non-specific esterase, and as the percentage of mature cells beyond the myelocyte stage which is visible after staining with May-Grünwald Giemsa. After culturing with the known 1α,25-DHCC or with vitamin D compounds of the invention, the percentage of cells containing black formazan deposits is determined. An increase in the percentage of NBT reducing cells indicates an increase in cell differentiation.

Proliferation and vitality of the cell cultures are established by counting the number of cells and by the trypan blue exclusion method. The vitality and proliferation of the cells in the HL-60 cultures are good in all conditions tested. 1α,25-DHCC (known), compound 12, compound 11, compound 13 and compound 14 all induce differentiation and maturation of the HL-60 cells. In the cytological test (non-specific esterase and May-Grünwald Giemsa) especially compounds 13 and 11 are good differentiators. The optimum effect is found at concentrations in the range of $10^{-8}$ to $10^{-7}$ M.

The NBT-reduction inducing capacity of compounds 13 and 14 is about 10× stronger than that of the known 1α,25-DHCC. Compounds 11 and 12 are about 5× more potent in inducing NBT-reduction than 1α,25-DHCC (FIGS. 3 and 4).

The above implies that the tested new vitamin D compounds of the invention display a higher cell differentiating activity than the known 1α,25-DHCC.

Figure 3:
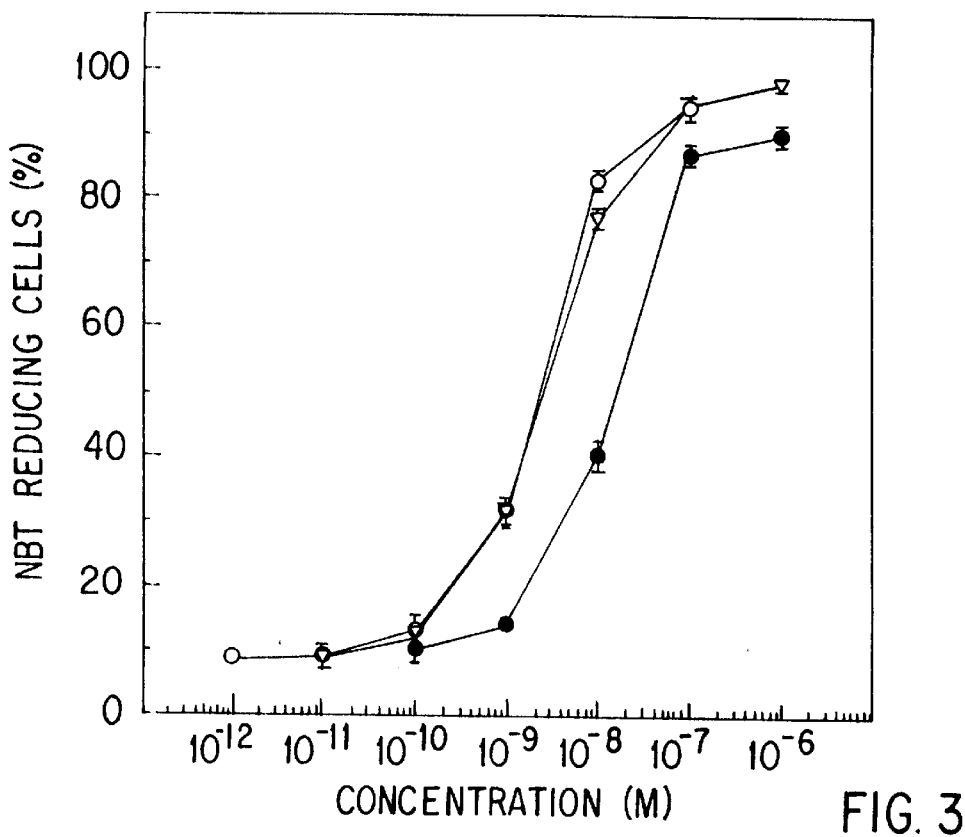
FIGS. 3 and 4 show the differentiating effect of vitamin D compounds on human leukemia cells of the HL-60 line, as per Example IX.
Figure 4:
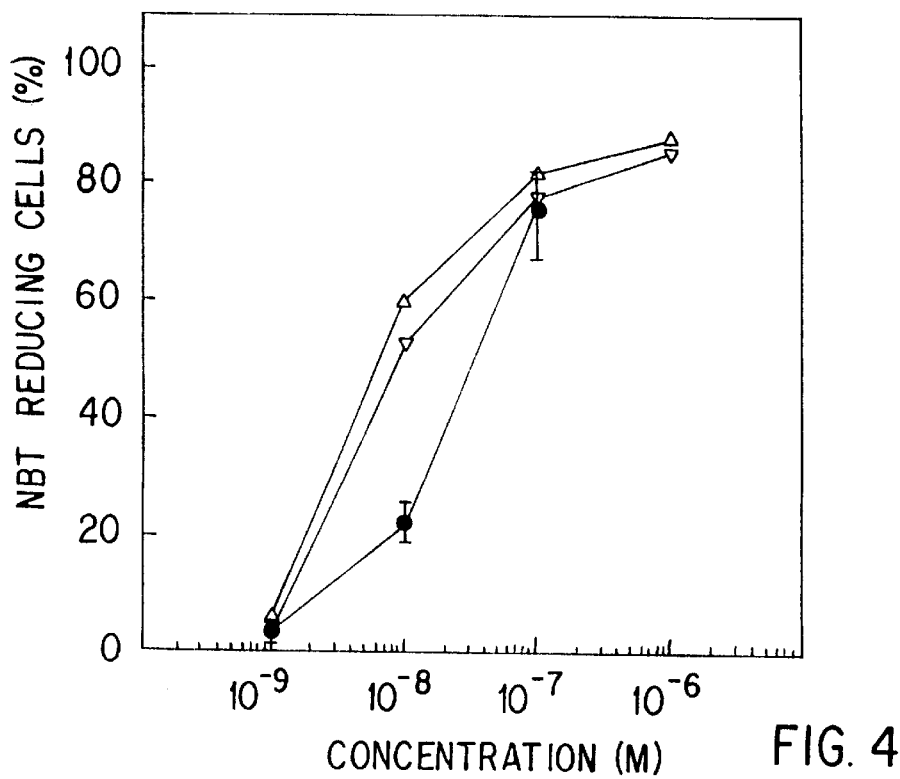

FIGS. 3 and 4 (appended) show the differentiating effect of the tested vitamin D compounds on human leukemia cells of the HL-60 line. In both FIGS. ●=1α,25-DHCC; in FIG. 3 ○ is compound 13 and ▽ is compound 14; in FIG. 4 Δ=compound 11 and ▽=compound 12.

Example X

Calciotropic Effect

The most well-known effects of 1α,25-DHCC is its action on the calcium metabolism, the calciotropic effect. Calciotropic target organs are the intestine, the bone and the kidney.

The vitamin D compounds according to the invention are dissolved in ethanol and tested in the so-called Caco-2 assay for intestinal calcium (Ca) transport. In this assay, the vitamin D-induced influx of $^{45}$Ca$^{2+}$ is measured in monolayers of the intestinal cancer cell line Caco-2.

This influx is corrected for the concentration-driven Ca$^{2+}$ influx and is a measure for the Ca transport across the intestinal wall. The Caco-2 cells are known to have vitamin D receptors.

Increased intestinal calcium transport can be the first step leading to a rise in blood calcium levels (and eventually to hipercalcemia).

In Table A below the effects of vitamin D compound, of the invention, compared with the known 1α,25-DHCC, on the Ca$^{2+}$ influx in intestinal Caco-2 cell cultures are presented. The values in the table represent the relative increase in Ca$^{2+}$ influx (the value for 1α,25-DHCC is arbitrarily fixed at 100).

The results in Table A demonstrate that compound 11, compound 13 and compound 14 are weaker stimulators of intestinal calcium absorption than 1α,25-DHCC.

TABLE A

| compound | $10^{-9}$ M |
|---|---|
| experiment 1 | |
| 1α,25-DHCC | 100 |
| compound 11 | 79 |
| compound 12 | 99 |
| experiment 2 | |
| 1α,25-DHCC | 100 |
| compound 13 | 65 |
| compound 14 | 78 |

Example XI

Calciotropic Effect

Together with the intestine and the bone, the kidney is one of the major target organs of 1α,25-DHCC. The kidney plays an extremely important role in calcium homeostasis, since about 98% of the calcium has to be reabsorbed in the kidneys in order to prevent calcium loss and hypocalcemia.

The vitamin D compounds according to the invention are dissolved in ethanol and tested in the rabbit kidney cell assey. In this assay, reabsorption of $^{45}$Ca$^{2+}$ is measured in monolayers of rabbit kidney cells.

The cells are isolated by immunodissection of connecting tubules with the aid of monoclonal antibodies.

In Table B below the effects of vitamin D compounds of the invention, compared with the known 1α,25-DHCC, on the Ca$^{2+}$-reabsorption in rabbit renal cell cultures are presented. The values in the Table represent the increase in Ca$^{2+}$-reabsorption in nmol/cm$^2$/h.

The results in Table B demonstrate that compound 13 and compound 11 are weaker stimulators of renal Ca-reabsorption than compound 12 and 1α,25-DHCC itself.

TABLE B

| compound   | $10^{-9}$ M |
|------------|-------------|
| 1α,25-DHCC | 13.4        |
| compound 11 | 2.4        |
| compound 12 | 12.8       |
| compound 13 | -3.7       |

Example XII

Cell Differentiation Versus Calciotropic Effect

One of the set-backs of the highly active vitamin D compounds, such as the well-known 1α,25-DHCC, is its calciotropic effect, which may lead to toxic hypercalciuria, hypercalcemia and urolithiasis. Therefore, it should be very advantageous to develop compounds with a high selectivity of biological action. In other words, compounds in which the ratio between the induction of cell differentiation and calciotropic effects, e.g. the stimulation of intestinal Ca transport, is changed compared to 1α,25-DHCC.

The ratio between differentiation-inducing capacity and the stimulation of intestinal Ca transport is defined as the fraction between the concentration at which 50% NBT reduction in HL-60 cells is obtained, and the concentration at which a half-maximal increase in intestinal $Ca^{2+}$ transport is reached. The smaller the ratio, the hiigher the relative cell differentiating capacity.

The results are presented in Table C.

TABLE C

| compound   | fraction | ratio relative to DHCC |
|------------|----------|------------------------|
| 1α,25-DHCC | 107      | 1.00                   |
| compound 12 | 29.7    | 0.28                   |
| compound 11 | 14.4    | 0.13                   |
| compound 14 | 2.6     | 0.02                   |
| compound 13 | 2.5     | 0.02                   |

Table C shows, that the tested new vitamin D compounds of the invention have better relative cell differentiating properties than the known 1α,25-DHCC. Compound 14 and compound 13 have 50× more selective actions than 1α,25-DHCC. Compound 11 has a 8× better ratio. Compound 12 has a 4× better ratio. This makes the new vitamin D compounds of the present invention extremely suitable for applications where the differentiation of cells (such as in hyperproliferative conditions) is desired.

We claim:
1. A vitamin D compound of the formula

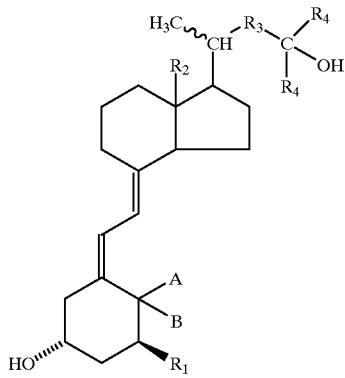

wherein:
  $R_1$ is hydroxy;
  $R_2$ is $CH_3$, $C_2H_5$, or —CH=$CH_2$;
  $R_3$ is —$(CH_2)_3$ or —$(CH_2)_4$—;
  $R_4$, which are identical, represent the isopropyl or cyclopropyl group; and
  A and B are each individually hydrogen atoms or methyl groups, or A and B form together a methylene group.

2. A vitamin D compound as claimed in claim 1, having the formula I shown in claim 1, wherein:
  $R_4$ is, a cyclopropyl group.

3. A vitamin D compound as claimed in claim 1, having the formula I shown in claim 1, wherein:
  $R_2$ has the meaning given in claim 1; and
  $R_4$ is an isopropyl group.

4. A pharmaceutical composition comprising, in addition to a pharmaceutically acceptable carrier and/or at least one pharmaceutically acceptable auxillary substance, as the active ingredient at least one compound as defined in claim 1, in an effective amount.

5. A composition an claimed in claim 4, in a dosage unit form, for oral, topical (dermal) or parenteral administration, comprising approx. 0.1 μg to approx. 0.1 mg active ingredient per dosis unit.

6. A composition for diagnostic purposes comprising, in addition to a compatible, non-toxic carrier and/or at least one auxillary substance, as the active ingredient at least one compound as defined in claim 1, in an effective amount.

7. A cosmetical composition, preferably selected from the group consisting of creams, lipocreams, lotions, ointments, liposomes and gels, comprising in addition to a cosmetically acceptable, non-toxic carrier and/or at least one auxillary substance, as the active ingredient at least one compound as defined in claim 1, in an effective amount.

8. A pharmaceutical composition comprising, in addition to a pharmaceutically acceptable carrier and/or at least one pharmaceutically acceptable auxiliary substance, as the active ingredient at least one compound as defined in claim 2 in a effective amount.

9. A pharmaceutical composition comprising, in addition to pharmaceutically acceptable carrier and/or at least one pharmaceutically acceptable auxiliary substance, as the active ingredient at least one compound as defined in claim 3 in a effective amount.

10. A composition as claimed in claim 8, in a dosage unit form, for oral, topical (dermal) or parenteral administration, comprising approximately 0.1 μg to approximately 0.1 mg active ingredient per dosis unit.

11. A composition as claimed in claim 9, in a dosage unit form, for oral, topical (dermal) or parenteral administration, comprising approximately 0.1 μg to approximately 0.1 mg active ingredient per dosis unit.

12. A composition for diagnostic purposes comprising, in addition to compatible, non-toxic carrier and/or at least one auxiliary substance, as the active ingredient at least one compound as defined in claim 2 in an effective amount.

13. A composition for diagnostic purposes comprising, in addition to compatible, non-toxic carrier and/or at least one auxiliary substance, as the active ingredient at least one compound as defined in claim 3 in an effective amount.

14. A cosmetical composition, preferably selected from the group consisting of creams, lipocreams, lotions, ointments, liposomes and gels, comprising in addition to a cosmetically acceptable, non-toxic carrier and/or at least one auxiliary substance, as the active ingredient at least one compound as defined in claim 2 in an effective amount.

15. A cosmetical composition, preferably selected from the group consisting of creams, lipocreams, lotions, ointments, liposomes and gels, comprising in addition to a cosmetically acceptable, non-toxic carrier and/or at least one auxiliary substance, as the active ingredient at least one compound as defined in claim 3 in an effective amount.

* * * * *